(12) United States Patent
Dalko et al.

(10) Patent No.: US 8,591,869 B2
(45) Date of Patent: Nov. 26, 2013

(54) ARYL C-XYLOSIDE COMPOUNDS, AND COSMETIC USE

(75) Inventors: Maria Dalko, Versailles (FR); Alexandre Cavezza, Pavillons Sous Bois (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/133,648

(22) PCT Filed: Dec. 11, 2009

(86) PCT No.: PCT/FR2009/052499
§ 371 (c)(1),
(2), (4) Date: Dec. 5, 2011

(87) PCT Pub. No.: WO2010/067036
PCT Pub. Date: Jun. 17, 2010

(65) Prior Publication Data
US 2012/0076743 A1 Mar. 29, 2012

Related U.S. Application Data

(60) Provisional application No. 61/140,294, filed on Dec. 23, 2008.

(30) Foreign Application Priority Data

Dec. 12, 2008 (FR) ..................... 08 58537

(51) Int. Cl.
*A61K 8/60* (2006.01)
(52) U.S. Cl.
USPC ......................................... 424/59
(58) Field of Classification Search
USPC ......................................... 424/59
See application file for complete search history.

(56) References Cited

U.S. PATENT DOCUMENTS

2004/0048785 A1 3/2004 Dalko et al.
2006/0223763 A1 10/2006 Dalko et al.

FOREIGN PATENT DOCUMENTS

WO WO 02/051828 A2 7/2002

OTHER PUBLICATIONS

International Search Report from the European Patent Office for International Application No. PCT/FR2009/052499, mailing date Jun. 4, 2010.
Bisht et al., "Aldol reaction of β-C-glycosylic ketones: synthesis of C-(E)-cinnamoyl glycosylic compounds as precursors for new biologically active C-glycosides", Carbohydrate Research 343 (2008) 1399-1406.
Bisht et al., "Synthetic studies in butenonyl C-glycosides: Preparation of polyfunctional alkanonyl glycosides and their enzyme inhibitory activity", Bioorganic & Medicinal chemistry Letters, 19 (2009) 2699-2703.

*Primary Examiner* — Jake Vu
(74) *Attorney, Agent, or Firm* — Novak Druce Connolly Bove + Quigg LLP

(57) ABSTRACT

The present invention relates to novel compounds of formula (I)

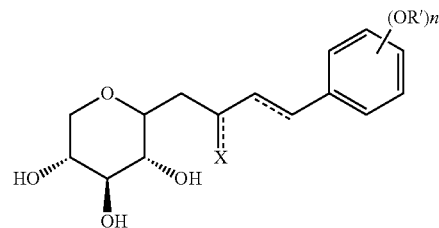

where:
X is an —OH or =O grouping;
n is an integer between 0 and 5;
R' is H or a $C_1$-$C_4$ alkyl radical,
when n≥2, two adjacent —OR' groupings can together form the divalent radical —O—$CH_2$—O—;
except when X=OH, the compound does not comprise a double ethylene link in the alpha position of the carbon having said OH.
The invention also relates to the salts thereof, to the optical isomers thereof, to the cosmetic and pharmaceutical compositions containing same, and to the use thereof to prevent and cosmetically treat the signs of aging on the skin.

19 Claims, No Drawings

ARYL C-XYLOSIDE COMPOUNDS, AND COSMETIC USE

The present invention relates to novel aryl C-xyloside derivatives, to the compositions, in particular cosmetic compositions, comprising the same, and also to the use thereof for combating skin aging.

Women and men currently have a tendency to wish to appear youthful for as long as possible and consequently seek to soften the signs of aging on the skin, which are reflected in particular by wrinkles and fine lines. In this respect, the media and the fashion world report about products intended to keep the skin radiant and wrinkle-free for as long as possible, which are signs of youthful skin, and all the more so since the physical appearance acts on the psyche and/or on the morale.

Up until now, wrinkles and fine lines were treated using cosmetic products containing active agents acting on the skin, for example by improving its cell renewal or alternatively by promoting the synthesis, or preventing the degradation, of the elastic fibers which make up the skin tissue.

It is known that human skin consists of two tissues, a surface tissue, the epidermis, and a deep tissue, the dermis.

Natural human epidermis is composed mainly of three types of cells: keratinocytes, which form the vast majority, melanocytes and Langerhans cells. Each of these cell types contributes, by virtue if its own functions, to the essential role played in the body by the skin, in particular the role of protecting the body against external attacks (climate, ultraviolet rays, tobacco, etc.), known as the "barrier function".

The dermis provides the epidermis with a solid support. It is also its feeder element. It consists mainly of fibroblasts and an extracellular matrix composed predominantly of collagen, elastin and a substance known as ground substance. These components are synthesized by the fibroblasts. Leucocytes, mast cells or else tissue macrophages are also found therein. Finally, blood vessels and nerve fibers pass through the dermis.

The extracellular matrix of the dermis is composed of proteins belonging to several major families: collagens, matrix glycoproteins other than collagens (fibronectin, laminin), elastin and proteoglycans. Glycosaminoglycans in free form (i.e. not bound to a protein) are also found in the extracellular matrix of the dermis.

It is now well established that specific interactions exist between these various classes of proteins so as to give rise to a functional tissue.

An extracellular space (micromatrix) also exists in the epidermis. This space plays an extremely important functional role in cell tissue renewal and/or maintenance.

Proteoglycans are complex macromolecules consisting of a branched central protein trunk, or protein network, to which a very large number of polysaccharide side chains known as glycosaminoglycans are attached.

In the remainder of the present application, the abbreviation PGs will be used to denote proteoglycans and the abbreviation GAGs will be used to denote glycosaminoglycans.

GAGs were for a long time referred to as acidic mucopolysaccharides owing to their high water-retaining capacity, their carbohydrate nature and their acidic nature originating from their multiple negative charges.

Thus, the polarity of GAGs makes them implicitly participate in certain biological functions such as tissue hydration, cation binding or an ionic filtration barrier role.

PGs and GAGs are synthesized by various cells in the dermis and the epidermis: fibroblasts, keratinocytes and melanocytes.

Fibroblasts synthesize predominantly collagens, matrix glycoproteins other than collagens (fibronectin, laminin), GAGs, proteoglycans and elastin. Keratinocytes synthesize predominantly sulfated GAGs and hyaluronic acid, while melanocytes do not apparently produce hyaluronic acid.

At the time of their incorporation into a PG, GAGs in the form of linear chains composed of repeats of a base disaccharide always containing a hexosamine (glucosamine or galactosamine) and another monosaccharide (glucuronic acid, iduronic acid or galactose). The glucosamine is either N-sulfated or N-acetylated. On the other hand, the galactosamine is always N-acetylated. In addition, there may be sulfate groups O-linked to the hexosamine, uronic acid and galactose.

The strong anionic nature of GAGs is explained by the presence of carboxylate groups within the hexuronic acids (glucuronic acid and iduronic acid) and of O- and N-linked sulfate groups.

The main GAGs are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS), which differs from the other glycosaminoglycans by the presence of galactose in place of uronic acid.

Proteoglycans (PGs) are formed by the anchoring of several GAG chains on a polypeptide chain (referred to as carrier protein or core protein).

GAGs can also exist in the extracellular matrix in free form, i.e. not bound to a matrix protein: this is in particular the case of hyaluronic acid.

When PGs are synthesized, the GAGs are polymerized from these anchoring structures.

The synthesis of GAGs requires the coordinated and concerted action of very specific enzymes (transferases, epimerases, sulfotransferases) which are adjacent in the membrane of the endoplasmic reticulum and of the golgi apparatus. A multitude of biochemical reactions (N-deacetylation, N- and O-sulfations, epimerization) then modify the two constituent monosaccharides of the base unit in a nonuniform manner along the chain. From one heparan sulfate chain to the other, for example, the glucuronic acid/iduronic acid ratio, the nature, the number and the position of the O-sulfations, and also the N-sulfate/O-sulfate ratio can vary, which potentially offers an immense structural diversity.

In general, the biological roles of PGs are very diversified, ranging from a passive function of mechanical support (for example serglycins) or a molecular filtration ionic barrier role (for example, perlecan and bamacan of the glomerular basal membrane), to more specific effects in cell adhesion, spreading, proliferation and differentiation or morphogenesis, or to highly specific effects of PG-protein interactions, such as the betaglycan receptor function or the interaction of decorin with collagen. They also play a fundamental role in the controlled release of various growth factors.

One of the roles of dermal connective tissue is to protect the body against external attacks while simultaneously forming an informative interface. To do this, the dermis has high mechanical strength while maintaining, however, great flexibility.

Its strength is provided by the dense network of collagen fibers, but it is the PGs and the hyaluronic acid which, by providing the moisturization, distribution and flexibility of the fibers, make the difference between the skin and, for example, leather.

The PGs constitute 0.5% to 2% of the dry weight of the dermis, collagen alone representing up to 80% thereof.

The concentration and distribution in human skin of GAGs and PGs vary with age.

Hyaluronic acid or hyaluronan (HA) is the main GAG of the dermis, the latter containing half the HA of the body.

The synthesis of HA is performed in particular by the fibroblasts, close to the inner face of the plasma membrane. It is performed continuously. This gigantic polysaccharide (several million daltons) has a very high intrinsic viscosity, ensuring the moisturization and assembly of the various components of the connective tissue by forming supramolecular complexes.

Dermatan sulfate (DS), which is first isolated in the dermis, is also very abundant in the skin. It constitutes 40% to 50% of the dermal GAGs.

In parallel with the mechanisms contributing to the development of these specialized extracellular matrices, continuous remodeling processes exist, the regulation of which depends on the balance between synthesis and degradation of the protein components of the matrix.

Several families of matrix proteases are now described, as are the factors involved in their activation-inactivation.

During chronological and/or photoinduced aging, the dermis and the epidermis undergo numerous modifications and degradations which are reflected, with age, by flaccidness and a loss of suppleness of the skin.

Among the components degraded (in particular collagen and elastin), the PGs and GAGs are also adversely affected. Specifically, during aging, the fibroblasts and the keratinocytes produce less and less PGs and GAGs and their synthesis is imperfect. This results in considerable disorganization: the deposition of GAGs on the protein backbone forming the PG is abnormal, the consequence of this being reduced avidity of these PGs for water and therefore a reduction in the moisturization and tonicity of tissues.

Restoring a normal production of PGs and GAGs by fibroblasts and keratinocytes contributes partially toward compensating for the loss of moisturization of the skin.

The degradation of these matrices thus contributes to the phenomenon of dryness and loss of suppleness of the skin.

The importance of having available products of which the effects are directed toward maintaining the level of PGs and GAGs in the skin and thus of maintaining, inter alia, good moisturization and good suppleness of the skin, can thus be appreciated.

It is known from document WO 02/051828 to use C-glycoside compounds for increasing the synthesis of glycosaminoglycans by fibroblasts and/or keratinocytes.

Other C-glycoside compounds for depigmenting the skin are also known from document WO 2006/128738.

The applicant has discovered, surprisingly and unexpectedly, that other aryl C-glycoside derivatives are capable of improving the synthesis of sulfated glycosaminoglycans such as chondroitin sulfate and dermatan sulfate.

Their effectiveness is greater than that of the C-glycoside compounds already known. They are more effective for improving epidermal renewal and firmness of the skin and for more effectively combating the signs of aging of the skin. They also have a beneficial effect on the structure of the dermal-epidermal junction, in particular on the cohesion between dermis and epidermis.

These novel compounds therefore find a particular application in cosmetic or pharmaceutical compositions, in particular dermatological compositions, intended for preventing and/or cosmetically treating aging of the skin; especially preventing and/or treating, in particular topically, the signs of aging on the skin, and most particularly the signs on the skin related to wrinkled skin, skin exhibiting a detrimental modification of its viscoelastic or biomechanical properties, skin exhibiting a detrimental modification in the cohesion of its tissues, thinned skin and/or skin exhibiting a detrimental modification of its surface appearance.

The compositions according to the invention can make it possible more particularly to maintain and/or restore the stretchability, tonicity, firmness, suppleness, density and/or elasticity properties of the skin.

The expression "biomechanical properties of the skin" is herein intended to mean the stretchability, tonicity, firmness, suppleness and/or elasticity properties of the skin.

The expression "signs of aging on the skin" is herein intended to mean any modification of the external appearance of the skin due to aging which is either chronobiological and/or extrinsic, in particular photoinduced or hormonal; among these signs, it is possible to distinguish:
wrinkled skin, which is reflected in particular by the appearance of wrinkles and/or fine lines,
skin exhibiting a detrimental modification of its viscoelastic or biomechanical properties, or skin exhibiting a lack of elasticity and/or of stretchability and/or of firmness and/or of suppleness and/or of tonicity, which is reflected in particular by wizened, flaccid or slack skin or skin that has sagged,
skin exhibiting a detrimental modification of the cohesion of its tissues,
thinned skin,
skin exhibiting a detrimental modification of its surface appearance, which is in particular reflected by a detrimental modification of the grain of the skin, for example a roughness.

A subject of the present invention is therefore novel amino C-glycoside compounds of formula (I) as defined hereinafter.

The invention also relates to a cosmetic or pharmaceutical composition comprising at least one such compound in a physiologically acceptable medium.

The compounds according to the invention therefore correspond to formula (I) below:

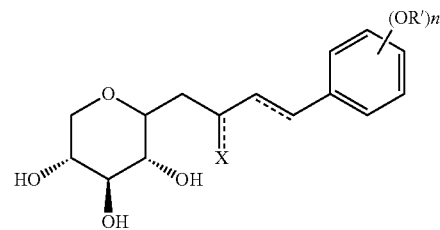

in which:
X denotes an —OH or =O group;
n is an integer ranging from 0 to 5;
R' denotes:
a hydrogen atom or
a linear $C_1$-$C_4$ or branched $C_3$-$C_4$ alkyl radical, or an unsaturated $C_3$-$C_4$ hydrocarbon-based radical,
when n≥2, two adjacent —OR' groups can together form the divalent radical —O—$CH_2$—O—;
with the proviso that, when X=OH, the compound does not comprise an ethylenic double bond in the alpha-position of the carbon bearing this OH;
and also the salts thereof, and the optical isomers thereof.

In the context of the present invention, the term "alkyl" means a saturated or unsaturated hydrocarbon-based chain. Among the alkyl groups suitable for implementation of the invention, mention may in particular be made of methyl, ethyl, isopropyl, n-propyl, n-butyl, t-butyl, isobutyl, sec-butyl, pentyl, hexyl, heptyl, octyl, nonyl and decyl groups.

Preferably,
X denotes an —OH or =O group;
n is an integer ranging from 0 to 3;

R' denotes:
a hydrogen atom or
a linear $C_1$-$C_4$ alkyl radical, in particular a methyl or n-butyl radical;
or a —CO—$CH_3$ radical;
when n≥2, two adjacent —OR' groups can together form the divalent radical —O—$CH_2$—O—.
Preferentially:
X denotes an —OH or =O group;
n is an integer ranging from 0 to 3;
R' denotes:
a hydrogen atom or
a methyl radical.

In particular, n and R' may be such that the aromatic part

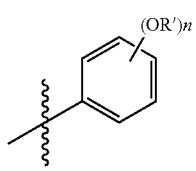

of the compounds of formula (I°) can correspond to one of the following structures:

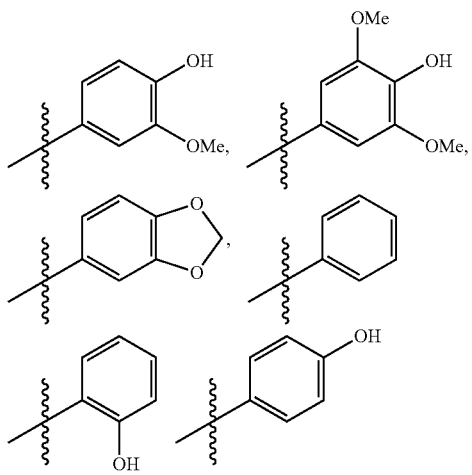

Mention may in particular be made of the following compounds of formula (I) (including the salts thereof or the solvates thereof):

1-($\alpha,\beta$)-D-xylopyranosyl-4-(4-hydroxy-3-methoxyphenyl) butan-2-ol (compound 1)

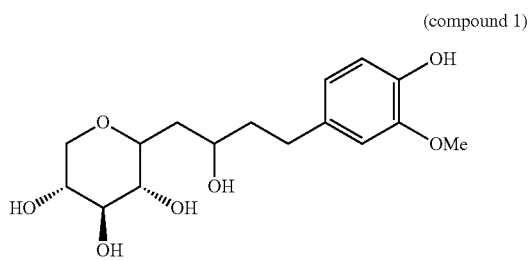 [SMILES: COc1cc(CCC(O)CC2OC[C@@H](O)[C@H](O)[C@H]2O)ccc1O]

1-($\alpha,\beta$)-D-xylopyranosyl-4-(4-hydroxy-3-methoxyphenyl) butan-2-one (compound 2)

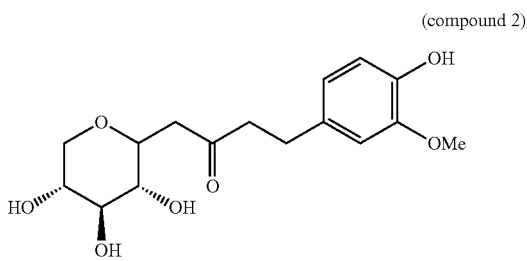 [SMILES: COc1cc(CCC(=O)CC2OC[C@@H](O)[C@H](O)[C@H]2O)ccc1O]

1-($\alpha,\beta$)-D-xylopyranosyl-4-(4-hydroxyphenyl)butan-2-ol (compound 3)

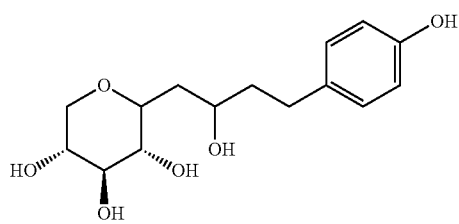

1-($\alpha,\beta$)-D-xylopyranosyl-4-phenylbutan-2-one (compound 4)

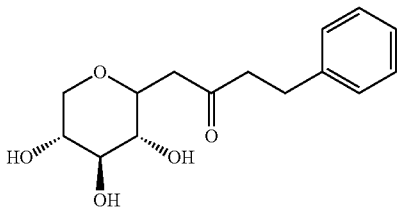

(3E)-1-($\alpha,\beta$)-D-xylopyranosyl-4-phenylbut-3-en-2-one (compound 5)

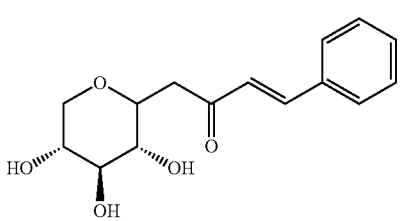

(3E)-1-($\alpha,\beta$)-D-xylopyranosyl-4-[4-hydroxy-(3,5)-dimethoxyphenyl]but-3-en-2-one (compound 6)

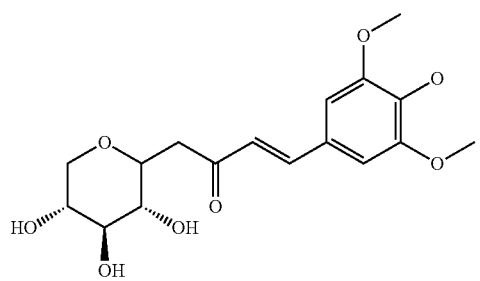

1-(α,β)-D-xylopyranosyl-4-[(3,4)-methylenedioxyphenyl]butan-2-ol (compound 7)

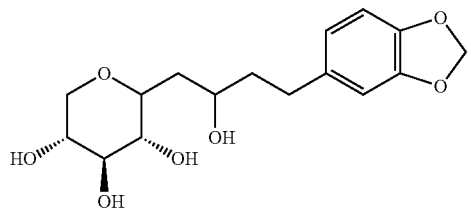

The acceptable solvates of the compounds described in the present invention comprise conventional solvates such as those formed during the last step of preparation of said compounds owing to the presence of solvents. By way of example, mention may be made of the solvates owing to the presence of water or of linear or branched alcohols such as ethanol or isopropanol.

The compounds of formula (I) can be prepared according to scheme I hereinafter:

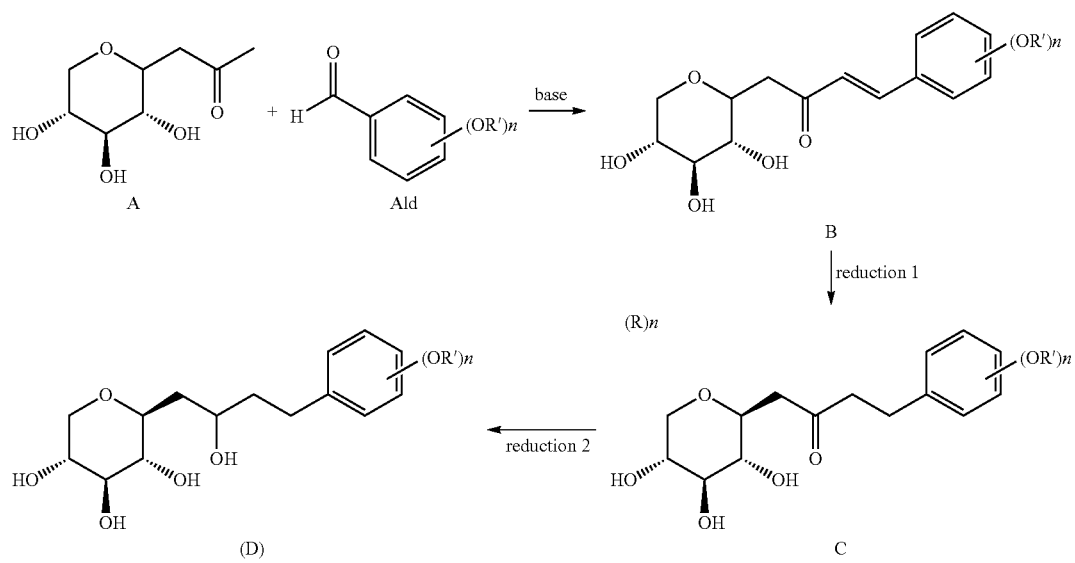

1-(α,β)-D-xylopyranosyl-4-(2-hydroxyphenyl)butan-2-ol (compound 8)

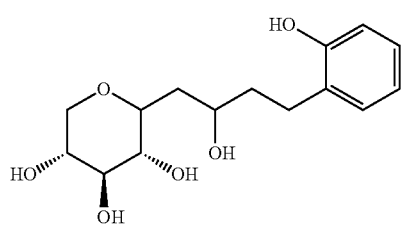

1-(α,β)-D-xylopyranosyl-4-phenylbutan-2-ol (compound 9)

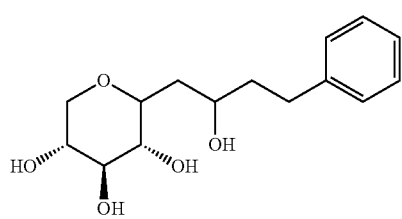

by reacting the C-β-D-xylopyranoside-n-propan-2-one (A) (compound described in example 1 of application WO 02/051828) with 1 to 2 equivalents of benzaldehyde of formula (III) (Ald) in which n and R' have the meanings as described above in the compounds of formula (I), in particular at ambient temperature (25° C.), in a polar solvent, such as water, ethanol, isopropanol or methanol, in the presence of a base (for example, sodium hydroxide or sodium methoxide), in particular for 1 to 20 hours.

The aldolization product (B) obtained can then be partially reduced in a known manner by catalytic hydrogenation (for example Pd/C/$H_2$) so as to obtain the compound (C). The compound (C) can in turn be continuously reduced by means of a hydride (for example sodium borohydride) or else by catalytic hydrogenation with palladium-on-carbon, followed by a step of hydrogenation in the presence of hydrogen under pressure, so as to obtain the compound (D). The compounds B, C and D are compounds in accordance with the structure of formula (I) described above.

The present invention also relates to a composition comprising, in a physiologically acceptable medium, a compound of formula (I) as described above. The composition is in particular a cosmetic or dermatological composition.

The compound of formula (I) may be present in the cosmetic or pharmaceutical compositions in an amount which can be between 0.01% and 10% by weight, preferably between 0.1% and 5% by weight, and in particular between 0.5% and 3% by weight, relative to the total weight of the composition.

The composition also comprises a physiologically acceptable medium, which will preferentially be a cosmetically or pharmaceutically, in particular dermatologically, acceptable medium, i.e. a medium which has no unpleasant odor, color or appearance, and which does not cause any tingling, tautness or redness unacceptable to the user. In particular, the composition is suitable for topical application to the skin.

The term "physiologically acceptable medium" is understood to mean a medium which is compatible with the keratin materials of human beings, such as bodily or facial skin, the lips, the mucous membranes, the eyelashes, the nails, the scalp and/or the hair.

The composition according to the invention may also comprise any of the cosmetic adjuvants normally used in the field of application envisioned.

Mention may in particular be made of water; organic solvents, in particular $C_1$-$C_6$ alcohols and $C_2$-$C_{10}$ carboxylic acid esters; hydrocarbon-based oils, silicone oils, fluoro oils, waxes, pigments, fillers, dyes, surfactants, emulsifiers, cosmetic or dermatological active agents, UV-screening agents, film-forming polymers, hydrophilic or lipophilic gelling agents, thickeners, preservatives, fragrances, bactericides, odor absorbers and antioxidants.

These optional adjuvants may be present in the composition in a proportion of from 0.001% to 80% by weight, in particular 0.1% to 40% by weight, relative to the total weight of the composition.

Depending on their nature, these adjuvants may be introduced into the fatty phase or into the aqueous phase of the composition, or into lipid vesicles. In any event, these adjuvants, and also the proportions thereof, will be chosen by those skilled in the art in such a way that the advantageous properties of the compounds according to the invention are not, or not substantially, impaired by the addition envisioned.

As oils that can be used in the invention, mention may be made of mineral oils (liquid petroleum jelly), oils of plant origin (avocado oil, soya oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax, ozokerite) can also be used as fats.

As hydrophilic gelling agents or thickeners, mention may be made of carboxyvinyl polymers (carbomer), acrylic copolymers, such as acrylate/alkyl acrylate copolymers, polyacrylamides, polysaccharides, natural gums and clays; as lipophilic gelling agents or thickeners, mention may be made of modified clays such as bentones, metal salts of fatty acids, and hydrophobic silica.

As active agents, it will be advantageous to introduce into the composition used according to the invention at least one compound chosen from: desquamating agents; moisturizing agents; depigmenting or propigmenting agents; anti-glycation agents; NO-synthase inhibitors; agents which stimulate the synthesis of dermal or epidermal macromolecules and/or prevent degradation thereof; agents which stimulate fibroblast and/or keratinocyte proliferation or stimulate keratinocyte differentiation; muscle relaxants and/or dermo-decontracting agents; tensioning agents; anti-pollution agents and/or free-radical scavengers; agents which act on the microcirculation; agents which act on the energy metabolism of cells; and mixtures thereof.

Examples of such additional compounds are: retinol and derivatives thereof, such as retinyl palmitate; ascorbic acid and derivatives thereof, such as magnesium ascorbyl phosphate and ascorbyl glucoside; tocopherol and derivatives thereof, such as tocopheryl acetate; nicotinic acid and precursors thereof, such as nicotinamide; ubiquinone; glutathione and precursors thereof, such as L-2-oxothiazolidine-4-carboxylic acid; plant extracts, and in particular plant proteins and hydrolysates thereof, and also phytohormones; marine extracts, such as algal extracts; bacterial extracts; sapogenins such as diosgenin and extracts of Wild Yam containing the same; ceramides; hydroxy acids, such as salicylic acid and 5-n-octanoylsalicylic acid; resveratrol; oligopeptides and pseudodipeptides and acylated derivatives thereof; manganese salts and magnesium salts, in particular gluconates; and mixtures thereof.

As indicated above, the composition according to the invention may also contain UV-screening agents or photoprotective agents which are active in the UVA and/or UVB range, in the form of organic or inorganic compounds, the latter being optionally coated so as to make them hydrophobic.

The organic photoprotective agents may in particular be chosen from: anthranilates, in particular menthyl anthranilate; benzophenones, in particular benzophenone-1, benzophenone-3, benzophenone-5, benzophenone-6, benzophenone-8, benzophenone-9, Ia benzophenone-12, and preferentially benzophenone-3 (oxybenzone), or benzophenone-4 (Uvinul MS40 from BASF); benzylidenecamphors, in particular 3-benzylidenecamphor, benzylidenecamphorsulfonic acid, camphor benzalkonium methosulfate, polyacrylamidomethylbenzylidenecamphor, terephthalylidenedicamphorsulfonic acid, and preferentially 4-methylbenzylidenecamphor (Eusolex 6300 from Merck); benzimidazoles, in particular benzimidazilate (Neo Heliopan AP from Haarmann and Reimer), or phenylbenzimidazole-sulfonic acid (Eusolex 232 from Merck); benzotriazoles, in particular drometrizole trisiloxane, or methylene[bis(benzotriazolyl)tetramethylbutyl]phenol (Tinosorb M from Ciba); cinnamates, in particular cinoxate, DEA methoxycinnamate, diisopropyl methylcinnamate, glycerylethylhexanoate dimethoxycinnamate, isopropyl methoxycinnamate, isoamyl cinnamate, and preferentially ethocrylene (Uvinul N35 from BASF), octyl methoxycinnamate (Parsol MCX from Hoffmann La Roche), or octocrylene (Uvinul 539 from BASF); dibenzoylmethanes, in particular butyl methoxydibenzoylmethane (Parsol 1789); imidazolines, in particular ethylhexyl dimethoxybenzylidene dioxoimidazoline; PABAs, in particular ethyldihydroxypropyl PABA, ethylhexyldimethyl PABA, glyceryl PABA, PABA, PEG-25 PABA, and preferentially diethylhexylbutamidotriazone (Uvasorb HEB from 3V Sigma), ethylhexyltriazone (Uvinul T150 from BASF), or ethyl PABA (benzocaine); salicylates, in particular dipropylene glycol salicylate, ethylhexyl salicylate, homosalate, or TEA salicylate; triazines, in particular anisotriazine (Tinosorb S from Ciba); drometrizole trisiloxane.

The inorganic photoprotective agents preferably consist of zinc oxide and/or titanium dioxide, preferably of nanometric size, optionally coated with alumina and/or with stearic acid.

This composition may be in any of the galenical forms normally used in the cosmetics or pharmaceutical field, and in particular in the form of an aqueous or aqueous-alcoholic, optionally gelled, solution, of a dispersion of the lotion type, which is optionally two-phase, of an emulsion obtained by dispersion of a fatty phase in an aqueous phase (O/W) or vice versa (W/O), or a triple emulsion (W/O/W or O/W/O) or of a vesicular dispersion of ionic and/or nonionic type, or of an aqueous or oily gel. These compositions are prepared according to the usual methods. A composition in the form of an emulsion, in particular an oil-in-water emulsion, is preferably used according to this invention.

The composition may be more or less fluid and may have the appearance of a white or colored cream, an ointment, a milk, a lotion, a serum, a paste, a gel or a foam. It may optionally be applied in the form of an aerosol. It may also be in solid form, in particular in the form of a stick.

When the composition is an emulsion, the proportion of the fatty phase may range from 5% to 80% by weight, preferably from 8% to 50% by weight, relative to the total weight of the composition. The emulsifier and the coemulsifier may be present in a proportion ranging from 0.3% to 30% by weight, and preferably from 0.5% to 20% by weight, relative to the total weight of the composition.

The composition according to the invention may constitute a skincare composition, in particular a cleansing, protection, treatment, or care cream for the face, for the hands, for the feet, for the major anatomical folds or for the body (for example, day creams, night creams, makeup-removing creams, foundation creams, antisun creams); a makeup-removing milk, a protective or care body milk, an antisun milk; a lotion, a gel or foam for skincare, such as a cleansing lotion.

The composition according to the invention is advantageously an anti-aging, in particular care, composition intended for treating and/or combating, cosmetically, the external signs of aging of the skin; the composition is more particularly a care composition for mature skin.

The composition may also be a makeup composition, in particular a foundation.

The invention also relates to a method for cosmetic treatment of the skin, comprising the application, to the skin, of a cosmetic composition as defined above. This method finds an advantageous application in treatment of the skin, in particular of mature skin and/or wrinkled skin, in particular of the face, especially of the forehead, the neck and/or the hands.

The invention also relates to the nontherapeutic cosmetic use of a cosmetic composition as defined above or of a compound of formula (I) as described above, for preventing and/or treating the signs of aging on the skin, in particular the signs of the skin chosen from wrinkled skin, skin exhibiting a detrimental modification of its viscoelastic or biomechanical properties, skin exhibiting a detrimental modification in the cohesion of its tissues, thinned skin, and skin exhibiting a detrimental modification of its surface appearance.

The invention also relates to the nontherapeutic cosmetic use of a composition as defined above or of a compound of formula (I) as described above, for improving the firmness of the skin and/or for improving the structure of the dermal-epidermal junction and/or for reinforcing the cohesion between the dermis and the epidermis.

The invention is illustrated in greater detail by the following nonlimiting examples.

EXAMPLE 1

Synthesis of 1-(α,β)-D-xylopyranosyl-4-(4-hydroxy-3-methoxy-phenyl)butan-2-one

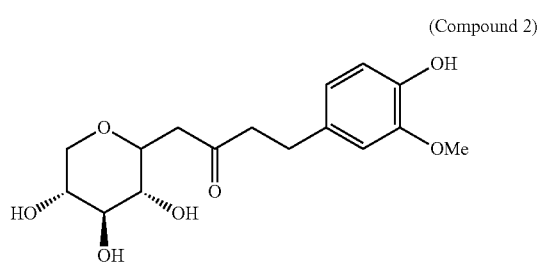 [SMILES: COc1cc(CCC(=O)CC2OC[C@@H](O)[C@H](O)[C@H]2O)ccc1O]

(Compound 2)

In 50 ml of anhydrous methanol, 5 g (1 eq) of C-β-D-xylopyranoside-n-propan-2-one were reacted with sodium methoxide at 30% in methanol (7.55 ml, 1.5 eq), and then 6.69 g (1.05 eq) of 4-benzyloxy-3-methoxybenzaldehyde were added.

The reaction medium was stirred for 15 hours at ambient temperature (25° C.), and was then diluted in dichloromethane and then washed with an aqueous solution of $NH_4Cl$. The organic phase was then dried over sodium sulfate and then concentrated under vacuum. The light brown oil obtained was purified on silica gel so as to obtain the corresponding intermediate (B) (pale yellow solid, yield of 30%).

The reaction intermediate (B) obtained (2 g, 1 eq) was solubilized in a water/ethanol mixture (5 ml/50 ml). Palladium-on-carbon at 10% (400 mg, 0.78 equivalent) was then added, as was cyclohexene (10 ml, 20.5 equivalents). The reaction medium was brought to reflux for 5 hours, and then left to cool to ambient temperature so as to be filtered and concentrated under vacuum. 1.57 g (1.57 g, slightly greenish-yellow oil) corresponding to compound 2 were thus obtained.

The $^1H$ NMR, $^{13}C$ NMR and mass spectra are in accordance with the structure of the expected product.

EXAMPLE 2

Synthesis of 1-(α,β)-D-xylopyranosyl-4-(4-hydroxy-3-methoxy-phenyl)butan-2-ol

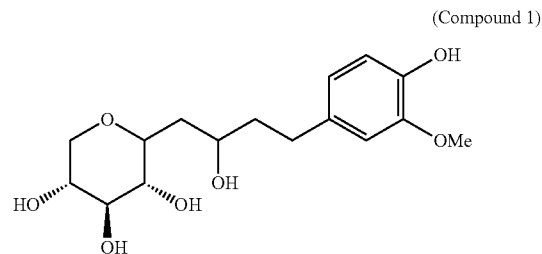 [SMILES: COc1cc(CCC(O)CC2OC[C@@H](O)[C@H](O)[C@H]2O)ccc1O]

(Compound 1)

The compound 2 obtained in example 1 (1.57 g, 1 eq) was solubilized in ethanol (20 ml) and then sodium borohydride (0.182 g, 1 eq) was added in small portions. The medium was stirred at ambient temperature for 12 hours. Acetone was then added in order to destroy the excess sodium borohydride, followed by aqueous hydrochloric acid (1N) in order to adjust the pH to 2. The reaction medium was then concentrated under vacuum, and the resulting product was taken up in water and then washed twice with ethyl acetate. The aqueous phase was then extracted with butanol, and the organic phases were combined and concentrated under vacuum. The crude product obtained was purified on silica gel, so as to obtain 0.53 g (yield of 34%) of a slightly yellow oil corresponding to the pure compound 1.

The $^1H$ NMR, $^{13}C$ NMR and mass spectra are in accordance with the structure of the expected product.

EXAMPLE 3

Synthesis of (3E)-1-(α,β)-D-xylopyranosyl-4-phenylbut-3-en-2-one

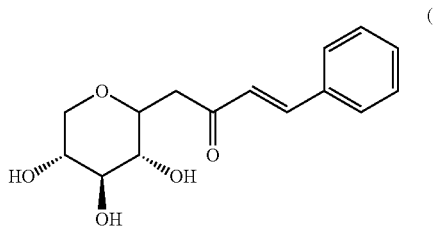

(Compound 5)

In 50 ml of ethanol, 2 g (10.5 mmol) of C-β-D-xylopyranoside-n-propan-2-one were reacted with 1.2 g (11.6 mmol) of benzaldehyde, and then 5.8 ml (15.8 mmol) of a solution of sodium methoxide at 21% in ethanol were added. The medium was stirred for one hour and then the reaction was stopped by adding a saturated solution of ammonium chloride.

The reaction medium was then concentrated under vacuum and taken up in water. The aqueous phase was extracted with butanol. The organic phases were dried and concentrated under vacuum. The crude product obtained was purified on silica gel, so as to obtain 700 mg (yield 25%) of the pure expected product in the form of a white solid.

The $^1$H NMR, $^{13}$C NMR and mass spectra are in accordance with the structure of the expected product.

EXAMPLE 4

Synthesis of 1-(α,β)-D-xylopyranosyl-4-phenylbutan-2-one

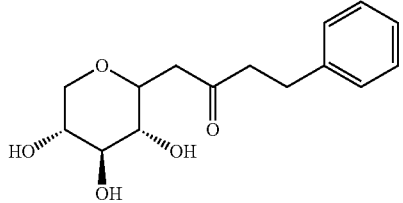

(Compound 4)

In a round-bottomed flask provided with a magnetic stirrer, 12 g of the compound 5 of example 3 were introduced into 70 ml of methanol, and 0.5 g of palladium-on-carbon at 10 mol % was added. The reaction mixture was stirred and placed under hydrogen pressure (100 000 Pa, i.e. 1 bar) for 15 hours. Next, the insoluble material was filtered off through a layer of celite, and the filtrate was evaporated under vacuum. 12 g (yield 99%) of compound 4 were obtained in the form of an off-white solid product.

EXAMPLE 5

Synthesis of: (compound 4): 1-(α,β)-D-xylopyranosyl-4-phenylbutan-2-ol

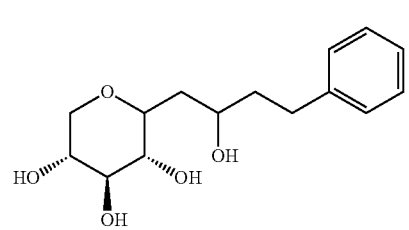

(Compound 9)

In a 250 ml round-bottomed flask, provided with a magnetic stirrer, 12 g (0.043 mol) of the compound 4 of example 4 were introduced, under nitrogen, into 100 ml of methanol. 1.954 g (0.0514 mol, 1.2 eq.) of sodium borohydride were then added in small portions with vigorous stirring at −20° C. At the end of the addition, the stirring was maintained for 10 minutes at 0° C., and then the mixture was hydrolyzed at this temperature, by means of HCl (3N) up to pH=4. The reaction mixture was then evaporated to dryness under vacuum. The residue obtained was diluted with acetone, and then filtered so as to remove the salts formed, and the filtrate was evaporated and then dried under vacuum. The crude product obtained was purified by flash chromatography on a silica column (eluent: ether, then acetone), so as to recover the expected compound 9 (yield 72%) in the form of off-white crystals.

EXAMPLE 6

Synthesis of 1-(α,β)-D-xylopyranosyl-4-(2-hydroxyphenyl)-butan-2-ol

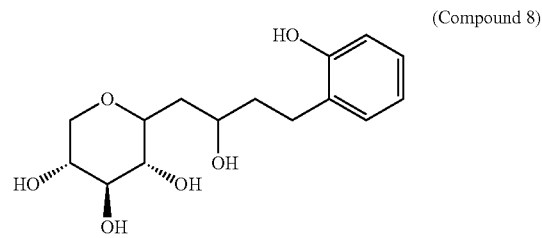 [SMILES: Oc1ccccc1CCC(O)CC1OC[C@@H](O)[C@H](O)[C@H]1O]

(Compound 8)

a) Synthesis of Compound A of Formula

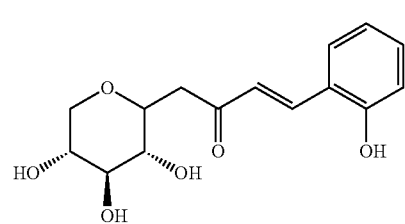

Compound A

C-β-D-Xylopyranoside-n-propan-2-one (1 equiv., 4.00 g) in solution in an ethanol (4.5 ml)+water (3.5 ml) mixture was treated with an aqueous solution of sodium hydroxide (3.5 equiv., 2.94 g, in 27 ml of water) at ambient temperature. After 2 hours of stirring, salicylaldehyde (1.2 equiv., 2.7 ml) was added dropwise at ambient temperature. After 20 hours of stirring, the pH was adjusted to 6 and then the reaction mixture was concentrated. The TLC analysis of the reaction crude revealed the formation of a largely predominant new product (Rf=0.38 for $CH_2Cl_2$/MeOH: 80/20)

Purification of this residue by silica column chromatography (solid deposit, $CH_2Cl_2$/MeOH: 80/20) makes it possible to recover the expected compound A in the form of an orange powder (4.27 g, yield=69%).

b) Synthesis of Compound B of Formula

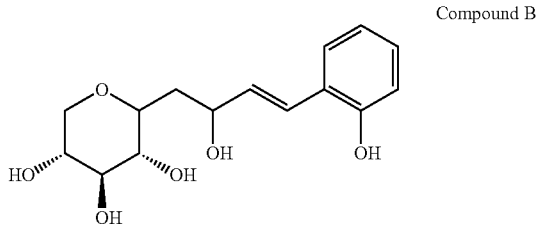 [SMILES: Oc1ccccc1/C=C/C(O)CC1OC[C@@H](O)[C@H](O)[C@H]1O]

Compound B

Compound A (1 equiv., 4.2 g) was dissolved in methanol (150 ml) and was then treated with $NaBH_4$ (2 equiv., 1.1 g), which was added at ambient temperature, portionwise, in order to limit the effervescence which occurs. The reaction mixture was stirred for 3 hours, after which time a TLC analysis of the reaction mixture revealed that the starting product had completely disappeared. The excess reducing agent was neutralized by adding a saturated aqueous solution of ammonium chloride (20 ml), and then the reaction mixture was concentrated. The reaction crude was purified by silica column chromatography (Rf=0.45 for $CH_2Cl_2$/MeOH: 80/20), so as to obtain compound B.

c) Synthesis of 1-(α,β)-D-xylopyranosyl-4-(2-hydroxyphenyl)butan-2-ol

Compound B (120 mg) was dissolved in 10 ml of ethanol, to which 3 drops of water were added, and was then hydrogenated at 30° C. using 10% Pd/C catalyst. After evaporation, the expected product is obtained in the form of a beige oil (60 mg, yield=49%).

EXAMPLE 7

Study of the Effect of C-Glycoside Derivatives on Sulfated Glycosaminoglycan Synthesis on Fibroblasts and on Keratinocytes The study is carried out by measuring the incorporation of radioactive glucosamine into the matrix neosynthesized by cultures of normal human dermal fibroblasts or by keratinocytes. The incorporation of radioactive glucosamine indicates specific neosynthesis of glycosaminoglycans via an incorporation of the acetylated form of this glucosamine.

The fibroblast cultures are performed according to conventional cell culture methods, namely in DMEM medium sold by the company Gibco, in the presence of L-glutamine (2 mM), of penicillin (50 IU/ml) and of 10% of fetal calf serum (Gibco).

The keratinocyte cultures are performed in keratinocyte-SFM medium sold by the company Gibco, in the presence of EGF (Epidermal Growth Factor) (0.25 ng/ml), of pituitary extract (25 μg/ml) and of gentamycin (25 μg/ml).

The fibroblasts and the keratinocytes were cultured in 96-well plates. At confluence, the culture medium was replaced with suitable culture medium containing or not containing (control) the test compound or the reference, and then the cells were incubated for 48 hours. The 35S-sulfate radioactive label was added (40 μCi final concentration) and the cells were incubated for a further 24 hours. All the conditions were carried out 3 times.

The extracellular matrix glycosaminoglycans were extracted with one volume of chaotropic buffer (50 mM Tris/HCl, 4 M guanidine, 5 mM, EDTA, pH 8.0).

The sulfated GAGs were purified by ion exchange chromatography: absorption of the anionic molecules onto Q-Sepharose beads under high-stringency conditions, desorption of the molecules which are not very anionic and molecules which are moderately anionic, with a 6 M urea solution containing 0.2 mM NaCl, and then washing.

The radioactivity incorporated into the highly cationic molecules that have remained on the support (predominantly GAGs) was measured by liquid scintillation.

The results are evaluated relative to a control consisting of cells which have not been treated with a compound of formula (I).

A positive control (TGF/3 at 10 ng/ml) known to stimulate GAG synthesis is introduced into the test carried out on fibroblasts, as a positive reference.

A positive control ($CaCl_2$ at 1.4 mM) known to stimulate GAG synthesis is introduced into the test carried out on keratinocytes, as a positive reference.

The results are expressed as percentage variation in glycosaminoglycan synthesis relative to the control.

3 tests were carried out for the tested compound.

The comparisons of the results obtained for a tested compound were carried out using the Student's test.

The standard deviation of the mean (sem) was calculated according to the following relationship:

$$\text{sem} = \text{standard deviation}/(n)^{1/2}$$

n being the number of tests carried out.

The results are given in the following table:

| | Mean value | sem | n | % | p |
|---|---|---|---|---|---|
| Treatment on fibroblasts | | | | | |
| Control (culture medium) | 2332 | 7 | 3-3 | 100-100 | 0.01 to 0.05 |
| Positive control (TGFβ) | 4062 | 9 | 3-3 | 174 | <0.001 |
| Compound of example 2  40 μM | 8130 | 28 | 3 | 351 | <0.001 |
| Compound of example 2  120 μM | 15318 | 22 | 3 | 657 | <0.001 |
| Treatment on keratinocytes | | | | | |
| Control (culture medium) | 4526 | 4 | 3-3 | 100-100 | 0.01 to 0.05 |
| Positive control ($CaCl_2$) | 5273 | 3 | 3-3 | 117 | 0.001 to 0.01 |
| Compound of example 2  0.37 mM | 31999 | 23 | 3 | 707 | <0.001 |
| Compound of example 2  1.1 mM | 36795 | 34 | 3 | 813 | <0.001 |

The values measured are given in counts per minute (cpm)
n: number of tests carried out
p: confidence interval
sem: standard deviation of the mean The results obtained show significantly that the compound of example 2 (compound 1) is very effective for increasing sulfated GAG synthesis.

This activity makes it possible to attribute to this compound a biological activity on the firmness of the skin, and thus to soften the signs of aging of the skin.

In another experimental plan, the compounds of example 5 (compound 9) and of example 6 (compound 8) were evaluated.

|  |  | Mean value | sem | n | % |
|---|---|---|---|---|---|
| Treatment on fibroblasts |  |  |  |  |  |
| Control (culture medium) |  | 2518 | 2 | 2 | 100 |
| Compound 8 of | 0.1 mM | 2938 | 13 | 2 | 117 |
| example 6 | 1 mM | 10371 | 34 | 2 | 412 |
| Compound 9 of | 0.1 mM | 10838 | 9 | 2 | 430 |
| example 5 | 1 mM | 23620 | 21 | 2 | 938 |
| Treatment on keratinocytes |  |  |  |  |  |
| Control (culture medium) |  | 4526 | 4 | 2 | 100 |
| Compound 8 of | 0.1 mM | 40552 | 40 | 2 | 316 |
| example 6 | 1 mM | 85456 | 47 | 2 | 665 |
| Compound 9 of | 0.1 μM | 24106 | 5 | 2 | 563 |
| example 5 | 1 μM | 99041 | 112 | 2 | 547 |

The results obtained show significantly that compounds 1, 8 and 91 are highly effective for increasing sulfated GAG synthesis.

This activity makes it possible to attribute to this compound a biological activity on the firmness of the skin, and thus to soften the signs of aging on the skin.

EXAMPLE 7

A face care cream of oil-in-water emulsion type is prepared, comprising (% by weight):

| Compound of example 2 | 0.005% |
|---|---|
| Glyceryl stearate | 2% |
| Polysorbate 60 (Tween 60 from ICI) | 1% |
| Stearic acid | 1.4% |
| Triethanolamine | 0.7% |
| Carbomer | 0.4% |
| Liquid fraction of shea butter | 12% |
| Perhydrosqualene | 12% |
| Antioxidant | qs |
| Fragrance, preservative | qs |
| Water | qs 100% |

A similar composition is prepared with the compound of examples 1 or 3 to 5.

The composition applied to the face makes it possible to reinforce the firmness of the skin and thus to soften the signs of aging on the skin.

EXAMPLE 8

An anti-aging gel for the skin is prepared, comprising (% by weight):

| Compound of example 2 | 2% |
|---|---|
| Hydroxypropylcellulose (Klucel H from Hercules) | 1% |
| Antioxidant | qs |
| Fragrance, preservative | qs |
| Isopropanol | 40% |
| Water | qs 100% |

A similar composition is prepared with the compound of examples 1 or 3 to 5.

The composition applied to the face makes it possible to reinforce the firmness of the skin and thus to soften the signs of aging on the skin.

The invention claimed is:

1. Compounds of formula (I):

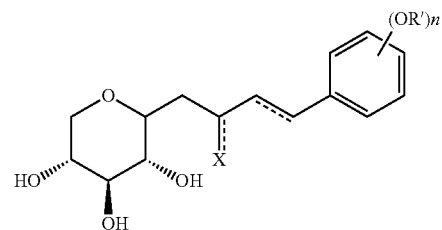

in which: X denotes an —OH or =O group;
n is an integer ranging from 0 to 5;
R' denotes: a hydrogen atom or a linear $C_1$-$C_4$ or branched $C_3$-$C_4$ alkyl radical, or an unsaturated $C_3$-$C_4$ hydrocarbon-based radical,
when n≥2, two adjacent —OR' groups can together form the divalent radical —O—$CH_2$—O—;
with the proviso that, when X=OH, the compound does not comprise an ethylenic double bond in the alpha-position of the carbon bearing this OH;
and also the salts thereof, and the optical isomers thereof.

2. The compounds as claimed in claim 1, in which:
X denotes an —OH or =O group;
n is an integer ranging from 0 to 3;
R' denotes: a hydrogen atom or
a linear $C_1$-$C_4$ alkyl radical;
or a —CO—$CH_3$ radical; when n≥2, two adjacent —OR' groups can together form the divalent radical —O—$CH_2$—O—.

3. The compounds as claimed in either of the preceding claims, in which:
X denotes an —OH or =O group;
n is an integer ranging from 0 to 3;
R' denotes: a hydrogen atom or
a methyl radical.

4. The compounds as claimed in claim 1, chosen from the following compounds:
1-(α,β)-D-xylopyranosyl-4-(4-hydroxy-3-methoxyphenyl)butan-2-ol;
1-(α,β)-D-xylopyranosyl-4-(4-hydroxy-3-methoxyphenyl)butan-2-1-one;
1-(α,β)-D-xylopyranosyl-4-(4-hydroxyphenyl)butan-2-ol;
1-(α,β)-D-xylopyranosyl-4-phenylbutan-2-one;
(3E)-1-(α,β)-D-xylopyranosyl-4-phenylbut-3-en-2-one;
(3E)-1-(α,β)-D-xylopyranosyl-4-[4-hydroxy-(3,5)-dimethoxyphenyl]but-3-en-2-one;
1-(α,β)-D-xylopyranosyl-4-[(3,4)-methylenedioxyphenyl]butan-2-ol;
1-(α,β)-D-xylopyranosyl-4-(2-hydroxyphenyl)butan-2-ol;
1-(α,β)-D-xylopyranosyl-4-phenylbutan-2-ol;
and the salts thereof or the solvates thereof.

5. A cosmetic or pharmaceutical composition comprising, in a physiologically acceptable medium, at least one compound of formula (I) as defined in claim 1.

6. The composition as claimed in claim 5, in which the compound of formula (I) is present, alone or as a mixture, in an amount of between 0.01% and 10% by weight relative to the total weight of the composition.

7. The composition as claimed in either of claims 5 and 6, in which the physiologically acceptable medium comprises at least one cosmetic adjuvant chosen from water;

organic solvents; hydrocarbon-based oils, silicone oils, fluoro oils, waxes, pigments, fillers, dyes, surfactants, emulsifiers, cosmetic or dermatological active agents, UV-screening agents, film-forming polymers, hydrophilic or lipophilic gelling agents, thickeners, preservatives, fragrances, bactericides, odor absorbers and antioxidants.

8. The composition as claimed in claim 5, in which the physiologically acceptable medium comprises at least one compound chosen from: desquamating agents; moisturizing agents; depigmenting or propigmenting agents; anti-glycation agents; NO-synthase inhibitors; agents which stimulate the synthesis of dermal or epidermal macromolecules and/or prevent degradation thereof; agents which stimulate fibroblast and/or keratinocyte proliferation or stimulate keratinocyte differentiation; muscle relaxants and/or dermo-decontracting agents; tensioning agents; anti-pollution agents and/or free-radical scavengers; agents which act on the microcirculation; agents which act on the energy metabolism of cells; and mixtures thereof.

9. The composition as claimed in claim 6, which is in the form of an anti-aging composition.

10. A method for nontherapeutic cosmetic treatment of the skin, comprising the application, to the skin, of a cosmetic composition as defined in claim 6.

11. The method as claimed in claim 10, in which the composition is applied to mature and/or wrinkled skin.

12. The nontherapeutic cosmetic treatment as defined in claim 10 which comprises improving the firmness of the skin and/or improving the structure of the dermal-epidermal junction and/or reinforcing the cohesion between the dermis and the epidermis.

13. The nontherapeutic cosmetic treatment composition as defined in claim 10, which comprises preventing and/or treating the signs of aging on the skin.

14. The compounds as claimed in claim 2, wherein said linear $C_1$-$C_4$ alkyl radical is a methyl or n-butyl radical.

15. The composition as claimed in claim 5, in which the compound of formula (I) is present, alone or as a mixture, in an amount of between 0.1% and 5% by weight.

16. The composition as claimed in claim 5, in which the compound of formula (I) is present, alone or as a mixture, in an amount of between 0.5% and 3% by weight.

17. The composition as claimed in claim 7, wherein said organic solvents are selected from the group consisting of $C_1$-$C_6$ alcohols and $C_2$-$C_{10}$ carboxylic acid esters.

18. The composition as claimed in claim 9, wherein the anti-aging composition is a care, composition intended for combating the external signs of aging of the skin.

19. The nontherapeutic cosmetic treatment composition as defined in claim 10, which comprises preventing and/or treating the signs of aging on the skin, wherein the signs on the skin are selected from the group consisting of wrinkled skin, skin exhibiting a detrimental modification of its viscoelastic or biomechanical properties, skin exhibiting a detrimental modification in the cohesion of its tissues, thinned skin, and skin exhibiting a detrimental modification of its surface appearance.

* * * * *

UNITED STATES PATENT AND TRADEMARK OFFICE
CERTIFICATE OF CORRECTION

PATENT NO. : 8,591,869 B2  Page 1 of 1
APPLICATION NO. : 13/133648
DATED : November 26, 2013
INVENTOR(S) : Maria Dalko et al.

It is certified that error appears in the above-identified patent and that said Letters Patent is hereby corrected as shown below:

**In the Claims:

At column 18, claim number 4, line numbers 54-55 please change as follows:
"1-(α,β)-D-xylopyranosyl-4-(4-hydroxy-3-methoxyphenyl)butan-2-one;"**

Signed and Sealed this
Fifteenth Day of September, 2015

Michelle K. Lee
*Director of the United States Patent and Trademark Office*